United States Patent
Cheng et al.

(10) Patent No.: US 12,403,358 B2
(45) Date of Patent: Sep. 2, 2025

(54) DATA PRE-PROCESSING METHOD AND EXERCISE VITAL SIGN DETECTION RADAR

(71) Applicant: Wistron Corporation, New Taipei (TW)

(72) Inventors: Kai-Jen Cheng, New Taipei (TW); Mn-Yu Chen, New Taipei (TW)

(73) Assignee: WISTRON CORPORATION, New Taipei (TW)

( * ) Notice: Subject to any disclaimer, the term of this patent is extended or adjusted under 35 U.S.C. 154(b) by 381 days.

(21) Appl. No.: 17/678,492

(22) Filed: Feb. 23, 2022

(65) Prior Publication Data

US 2023/0136937 A1   May 4, 2023

(30) Foreign Application Priority Data

Oct. 29, 2021 (TW) .................................. 110140489
Oct. 29, 2021 (TW) .................................. 110140492

(51) Int. Cl.
| | |
|---|---|
| *A63B 24/00* | (2006.01) |
| *G01S 7/35* | (2006.01) |
| *G01S 7/41* | (2006.01) |
| *G16H 50/20* | (2018.01) |

(52) U.S. Cl.
CPC .......... *A63B 24/0062* (2013.01); *G01S 7/354* (2013.01); *G01S 7/356* (2021.05); *G01S 7/358* (2021.05); *G01S 7/412* (2013.01); *G16H 50/20* (2018.01); *A63B 2220/89* (2013.01)

(58) Field of Classification Search
CPC ............ A63B 24/0062; A63B 2220/89; G16H 50/20; G01S 7/356; G01S 7/358; G01S 7/354; G01S 7/412
See application file for complete search history.

(56) References Cited

U.S. PATENT DOCUMENTS

| | | | |
|---|---|---|---|
| 10,374,863 B2 | 8/2019 | Xu et al. | |
| 10,576,328 B2 | 3/2020 | Santra et al. | |
| 10,617,330 B1 | 4/2020 | Joshi et al. | |
| 2008/0024785 A1* | 1/2008 | Froggatt | G01M 11/3172 |
| | | | 356/450 |
| 2019/0007256 A1 | 1/2019 | Chen et al. | |
| 2019/0104954 A1 | 4/2019 | Campbell et al. | |

(Continued)

FOREIGN PATENT DOCUMENTS

| | | |
|---|---|---|
| CN | 109188414 A | 1/2019 |
| CN | 109740522 A | 5/2019 |

(Continued)

OTHER PUBLICATIONS

Examination report dated Apr. 11, 2022, listed in related Taiwan patent application No. 110140489.

(Continued)

*Primary Examiner* — Vladimir Magloire
(74) *Attorney, Agent, or Firm* — McClure, Qualey & Rodack, LLP

(57) ABSTRACT

A data pre-processing method is provided. By using an energy distribution parameter set obtained through beamforming scanning, a signal-to-noise ratio of a signal can be improved and a detection range region can be automatically generated, thereby improving an object tracking effect. An exercise vital sign detection radar is also provided.

17 Claims, 14 Drawing Sheets

(56) References Cited

U.S. PATENT DOCUMENTS

| | | | |
|---|---|---|---|
| 2019/0142289 A1 | 5/2019 | Bliss et al. | |
| 2019/0212429 A1 | 7/2019 | Yamanouchi | |
| 2019/0212436 A1 | 7/2019 | Baheti et al. | |
| 2019/0216393 A1 | 7/2019 | Baheti et al. | |
| 2020/0041610 A1* | 2/2020 | Longman | G01S 13/931 |
| 2020/0103516 A1 | 4/2020 | Kim et al. | |
| 2020/0116824 A1 | 4/2020 | Yang et al. | |
| 2020/0155038 A1 | 5/2020 | Katabi et al. | |
| 2020/0180472 A1 | 6/2020 | Lu-Dac et al. | |
| 2020/0191913 A1* | 6/2020 | Zhang | G01S 7/412 |
| 2021/0045651 A1* | 2/2021 | Li | A61B 5/7257 |
| 2021/0093203 A1 | 4/2021 | Zhong et al. | |
| 2021/0109208 A1 | 4/2021 | Tzyy-Sheng et al. | |
| 2021/0197834 A1* | 7/2021 | Shaker | G01S 7/354 |

FOREIGN PATENT DOCUMENTS

| | | | | |
|---|---|---|---|---|
| CN | 110450784 A | | 11/2019 | |
| CN | 110946555 A | | 4/2020 | |
| CN | 110946587 A | | 4/2020 | |
| CN | 106821347 B | | 5/2020 | |
| CN | 111142102 A | | 5/2020 | |
| CN | 111812633 A | | 10/2020 | |
| CN | 112263242 A | * | 1/2021 | |
| CN | 112386237 A | | 2/2021 | |
| CN | 112560803 A | * | 3/2021 | |
| CN | 113281739 A | | 8/2021 | |
| CN | 114647009 A | * | 6/2022 | |
| DK | 202070213 A | * | 12/2002 | G01S 13/18 |
| EP | 2428814 A1 | * | 3/2012 | G01S 13/04 |
| EP | 3 901 651 A1 | | 10/2021 | |
| KR | 20180089427 A | * | 8/2018 | |
| WO | 2018031516 A1 | | 2/2018 | |
| WO | 2018183546 A1 | | 10/2018 | |
| WO | 2018206934 A1 | | 11/2018 | |
| WO | 2019070651 A1 | | 4/2019 | |
| WO | 2019079855 A1 | | 5/2019 | |
| WO | 2019122412 A1 | | 6/2019 | |
| WO | 2019122413 A1 | | 6/2019 | |
| WO | 2019144413 A1 | | 8/2019 | |
| WO | 2020102813 A1 | | 5/2020 | |
| WO | 2020104465 A2 | | 5/2020 | |

OTHER PUBLICATIONS

Exercise Vital Signs Detection Employing FMCW Radar and Artificial Neural Networks; 2020.

Music-based algorithm for range-azimuth FMCW radar data processing without estimating number of targets; 2015.

Takuya Sakamoto, etc., "Noncontact Measurement of the Instantaneous Heart Rate in a Multi-Person Scenario Using X-Band Array Radar and Adaptive Array Processing", IEEE Journal on Emerging and Selected Topics and Systems, vol. 8, No. 2, IEEE, Jun. 2018 Abstract, Figure 1, Papers I., IV, VI, VII.

Examination report dated Jan. 15, 2024, listed in related Taiwan patent application No. 110140492.

Examination report dated Jun. 23, 2022, listed in related Taiwan patent application No. 110140492.

Extended European Search Report dated Oct. 10, 2022, listed in related European patent application No. 22 172 256.4.

* cited by examiner

Frequency (bpm)

Difference

DATA PRE-PROCESSING METHOD AND EXERCISE VITAL SIGN DETECTION RADAR

CROSS-REFERENCES TO RELATED APPLICATIONS

This non-provisional application claims priority under 35 U.S.C. § 119(a) to Patent Application No. 110140489 filed in Taiwan, R.O.C. on Oct. 29, 2021 and Patent Application No. 110140492 filed in Taiwan, R.O.C. on Oct. 29, 2021, the entire contents of which are hereby incorporated by reference.

BACKGROUND

Technical Field

The present invention relates to radar signal processing technologies, and in particular, to a radar signal data pre-processing method and an exercise vital sign detection radar to which the method is applied for detection.

Related Art

There are many wearable or direct-contact vital sign parameter measurement devices that can monitor vital sign parameters (such as a heart rate) in activities of daily living. However, wearing a wearable or contact device for a long time makes a subject feel uncomfortable. Although there are still non-contact measurement manners, when the subject is in an exercise state, the shaking of the body of the subject is apt to interfere with measurement, to affect the accuracy of the measurement.

SUMMARY

In view of this, according to some embodiments, a data pre-processing method is provided, performed by a processor in a signal processing apparatus, the method including: obtaining an energy distribution parameter set obtained through beamforming scanning and a digital signal, where the digital signal corresponds to a reflected radar signal of an exercise vital sign detection radar; searching, by using the energy distribution parameter set, for a target in a manner of filtering out background noise; weighting the digital signal according to the energy distribution parameter set to obtain an optimized signal; analyzing the optimized signal to extract one or more pieces of target phase data corresponding to the target from the optimized signal; and inputting the one or more pieces of target phase data into a machine learning model to obtain a vital sign parameter prediction result.

According to some embodiments, an exercise vital sign detection radar is provided, including: a transmitting unit, a receiving unit, and a signal processing module. The transmitting unit is configured to transmit an incident radar signal. The receiving unit is configured to receive a reflected radar signal. The signal processing module is configured to control the transmitting unit and the receiving unit to perform beamforming scanning to obtain an energy distribution parameter set, obtain a corresponding digital signal according to the reflected radar signal, search, by using the energy distribution parameter set, for a target in a manner of filtering out background noise, weight the digital signal according to the energy distribution parameter set to obtain an optimized signal, analyze the optimized signal to extract one or more pieces of target phase data corresponding to the target from the optimized signal, and input the one or more pieces of target phase data into a machine learning model to obtain a vital sign parameter prediction result.

According to some embodiments, a data pre-processing method is provided, performed by a processor in a signal processing apparatus, the method including: obtaining an energy distribution parameter set obtained through beamforming scanning and a digital signal, where the digital signal corresponds to a reflected radar signal of an exercise vital sign detection radar; searching, by using the energy distribution parameter set, for a target in a manner of filtering out background noise; analyzing the digital signal to extract one or more pieces of target phase data corresponding to the target from the digital signal; dividing the one or more pieces of target phase data into a plurality of sub-bands through wavelet transform; performing statistical analysis on each of the sub-bands to obtain a statistical characteristic set; and inputting the statistical characteristic set into a machine learning model to obtain a vital sign parameter prediction result.

According to some embodiments, statistics on the energy distribution parameter set in a period are collected to determine a detection range region covering an activity range of the target, to further analyze the optimized signal in the detection range region.

According to some embodiments, signal processing including phase difference calculation and pulse noise removal is further performed on the one or more pieces of target phase data before the one or more pieces of target phase data are inputted into the machine learning model.

According to some embodiments, a phase map and a vibration frequency map are obtained according to the optimized signal. Furthermore, at least one candidate position having an energy intensity exceeding an energy threshold is selected from the vibration frequency map. A target position is selected from the at least one candidate position, where the target position is a position that has a vibration frequency meeting a vital sign parameter range in the at least one candidate position and has the highest energy intensity. Subsequently, the one or more pieces of target phase data in a distance range in the phase map are obtained according to the target position. The phase map presents an energy distribution with a distance change relative to the exercise vital sign detection radar and a phase change, and the vibration frequency map presents an energy distribution with the distance change relative to the exercise vital sign detection radar and a vibration frequency change.

According to some embodiments, statistics on the energy distribution parameter set in a period are collected to determine a detection range region covering an activity range of the target, where the step of selecting the at least one candidate position is selecting the at least one candidate position from the detection range region in the vibration frequency map.

According to some embodiments, Fast Fourier Transform (FFT) is performed on the optimized signal to obtain a range profile map. Direct current (DC) bias removal, in-phase and quadrature-phase (IQ) imbalance compensation, arctangent, and phase unwrapping are performed on ranges on the range profile map with the time change to obtain the phase map. FFT is performed on phase distributions on ranges on the phase map to obtain the vibration frequency map. The range profile map presents an energy distribution with the distance change relative to the exercise vital sign detection radar and a time change.

According to some embodiments, the energy threshold is calculated for each range bin in the phase map, where the energy threshold is determined according to an average energy value or a maximum energy value of the corresponding range bin. Furthermore, energy values of phases on the each range bin are separately compared with the energy threshold corresponding to the range bin, to select the at least one candidate position having an energy intensity exceeding the energy threshold.

According to some embodiments, a phase map and a vibration frequency map are obtained according to the optimized signal, and at least one candidate position having an energy intensity exceeding an energy threshold is selected from the vibration frequency map; N to-be-detected target positions are selected from the at least one candidate position, where N is greater than 1, and the N to-be-detected target positions are positions that have a vibration frequency meeting a vital sign parameter range in the at least one candidate position and have top N energy intensities; and subsequently, the one or more pieces of target phase data in a corresponding distance range in the phase map are obtained according to each of the target positions. The phase map presents an energy distribution with a distance change relative to the exercise vital sign detection radar and a phase change, and the vibration frequency map presents an energy distribution with the distance change relative to the exercise vital sign detection radar and a vibration frequency change.

Based on the above, through the data pre-processing method and the exercise vital sign detection radar according to some embodiments, vital sign parameters can be accurately detected when a subject is in an exercise state and the exercise intensity of the subject can be detected. In some embodiments, by weighting the digital signal, a signal-to-noise ratio can be increased. In some embodiments, by automatically generating the detection range region, calculation complexity can be reduced and an object tracking effect can be improved. In some embodiments, through signal processing to reduce noise, noise interference can be reduced. In some embodiments, by performing machine-learning prediction by using the statistical characteristic set, model training and prediction can be accelerated.

DETAILED DESCRIPTION

A term "connect" used in this specification means that two or more elements are in physical or electrical contact with each other directly, or are in physical or electrical contact with each other indirectly.

Figure 1:
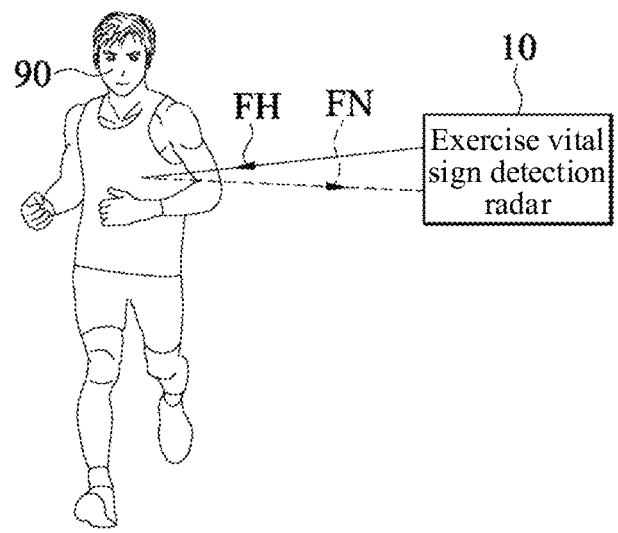
FIG. 1 is a schematic diagram of a use state of an exercise vital sign detection radar according to some embodiments.

FIG. 1 is a schematic diagram of a use state of an exercise vital sign detection radar 10 according to some embodiments. The exercise vital sign detection radar 10 transmits a radar signal (hereinafter referred to as "incident radar signal FH"). The incident radar signal FH is transmitted to a target 90, modulated due to the exercise of the target 90 (for example, a subject), and reflected to the exercise vital sign detection radar 10. The radar signal that is reflected is referred to as "reflected radar signal FN" hereinafter. Therefore, one or more types of information of the target 90 can be detected by analyzing the reflected radar signal FN. The information may be, for example, speed, distance, orientation, vital sign information (such as heartbeat, or respiration), and the like.

In some embodiments, the exercise vital sign detection radar 10 may be an FMCW radar, a continuous wave (CW) radar, or an ultra-wideband (UWB) radar. Descriptions are made below by using an FMCW radar as an example.

Figure 2:
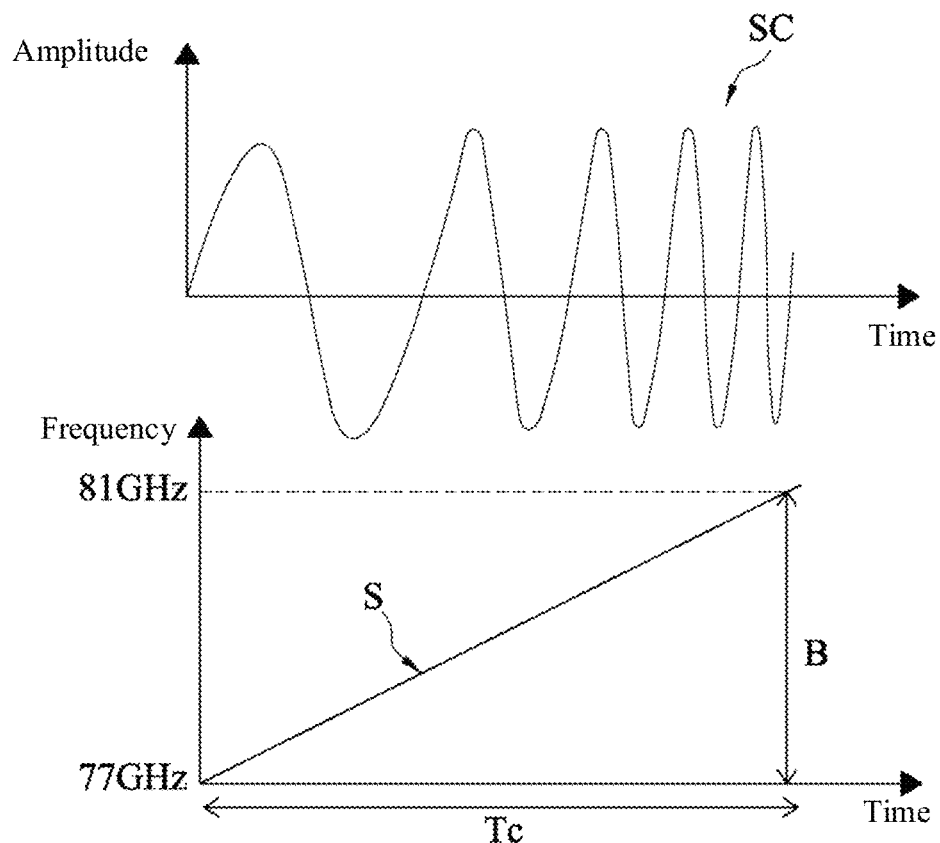
FIG. 2 is a schematic diagram of illustrating a radar signal.

FIG. 2 is a schematic diagram of illustrating a radar signal. An upper half shows a change of an amplitude of the incident radar signal FH with time, and a lower half shows a change of a frequency of the incident radar signal FH with time. The incident radar signal FH includes a plurality of chirped signals SC. FIG. 2 shows only one chirped pulse SC for clarity. The chirped pulse SC is a linear frequency modulation pulse signal, which refers to a sine wave with a frequency increasing in a linear manner with time. In some embodiments, a frequency of the chirped pulse SC increases in a nonlinear manner. For ease of description, descriptions are made below by using a linear manner. As shown in FIG. 2, within a duration Tc (for example, 40 microseconds), the chirped pulse SC linearly increases from a start frequency (for example, 77 GHz) to a stop frequency (for example, 81 GHz) according to a slope S. The start frequency and the stop frequency may be selected from a millimeter wave frequency band (namely, 30 GHz to 300 GHz). A difference between the start frequency and the stop frequency is a pulse bandwidth B.

Figure 3:
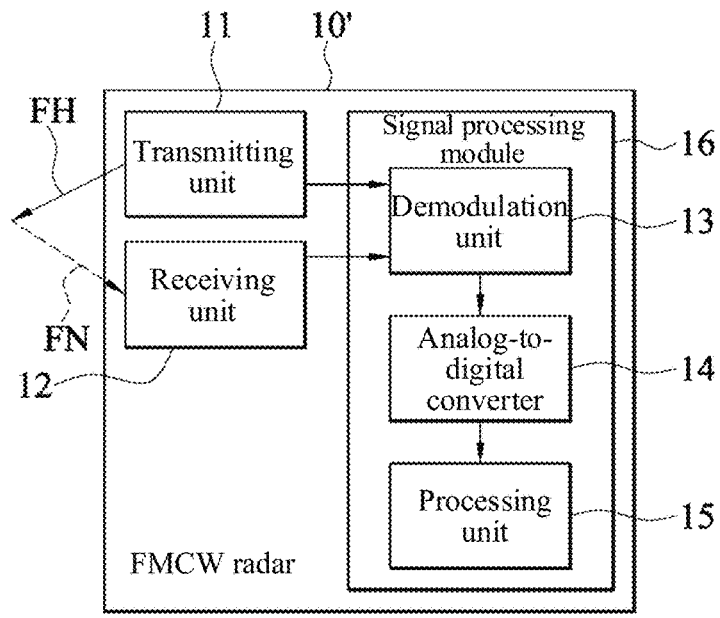
FIG. 3 is a schematic block diagram of a frequency modulated continuous wave (FMCW) radar according to some embodiments.
Figure 4:
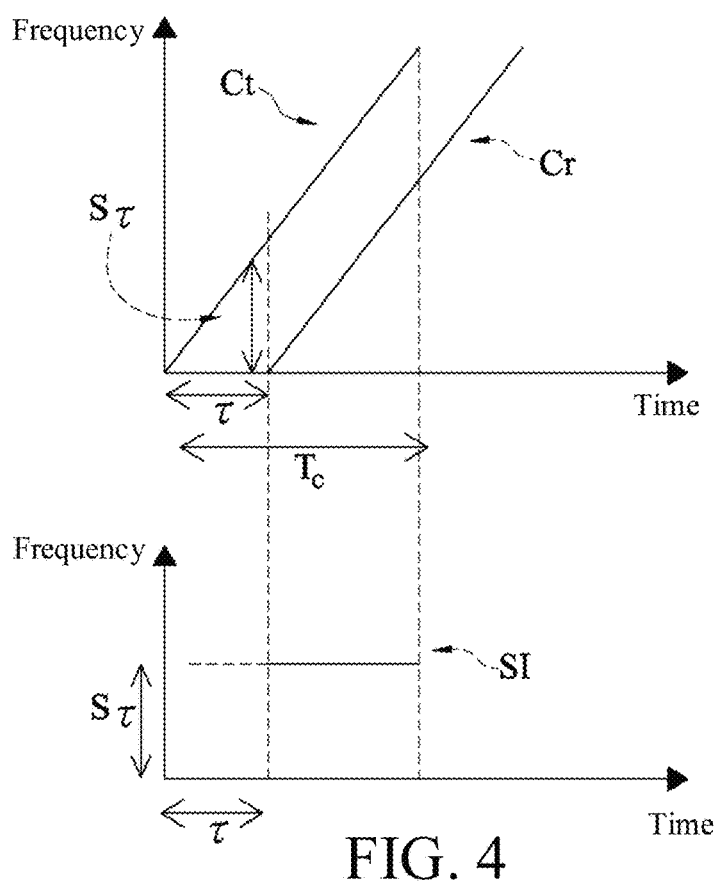
FIG. 4 is a schematic diagram of illustrating an incident radar signal and a reflected radar signal.

Refer to FIG. 3 and FIG. 4 together. FIG. 3 is a schematic block diagram of an FMCW radar 10' according to some embodiments. FIG. 4 is a schematic diagram of illustrating an incident radar signal FH and a reflected radar signal FN. The FMCW radar 10' includes a transmitting unit 11, a receiving unit 12, a demodulation unit 13, an analog-to-digital converter 14, and a processing unit 15. The transmitting unit 11 is configured to transmit the incident radar signal FH, and includes a transmitting antenna and a signal synthesizer. The signal synthesizer is configured to generate the incident radar signal FH including a chirped pulse Ct, and the incident radar signal FH is transmitted by using the transmitting antenna. The receiving unit 12 includes a receiving antenna configured to receive the reflected radar signal FN including at least one chirped pulse Cr. The chirped pulse Cr may be regarded as a delayed chirped pulse Ct. The demodulation unit 13, the analog-to-digital converter 14, and the processing unit 15 are configured to process the received reflected radar signal FN, and may be collectively referred to as a signal processing module 16. The demodulation unit 13 is connected to the transmitting unit 11 and the receiving unit 12, and includes a mixer and a low-pass filter. The mixer couples the chirped pulse Ct of the incident radar signal FH and the chirped pulse Cr corresponding to the reflected radar signal FN, which can generate two coupled signals such as a sum of a frequency of the chirped pulse Ct and a frequency of the chirped pulse Cr, and a difference between the frequency of the chirped pulse Ct and the frequency of the chirped pulse Cr. The low-pass filter performs low-pass filtering on the coupled signals to remove a high-frequency component to obtain the coupled signal of the difference between the frequency of the chirped pulse Ct and the frequency of the chirped pulse Cr, which is hereinafter referred to as "intermediate frequency signal SI". The analog-to-digital converter 14 connects between the demodulation unit 13 and the processing unit 15. The analog-to-digital converter 14 converts the intermediate frequency signal SI into a digital signal. The processing unit 15 performs digital signal processing on the digital signal. The processing unit 15 may be, for example, a central processing unit (CPU), a graphics processing unit (GPU), or a microprocessor, a digital signal processor (DSP), a programmable controller, an application-specific integrated circuit (ASIC), or a programmable logic device (PLD) with general purposes or special purposes, or other similar apparatuses, chips, integrated circuits, or a combination thereof.

Figure 21:
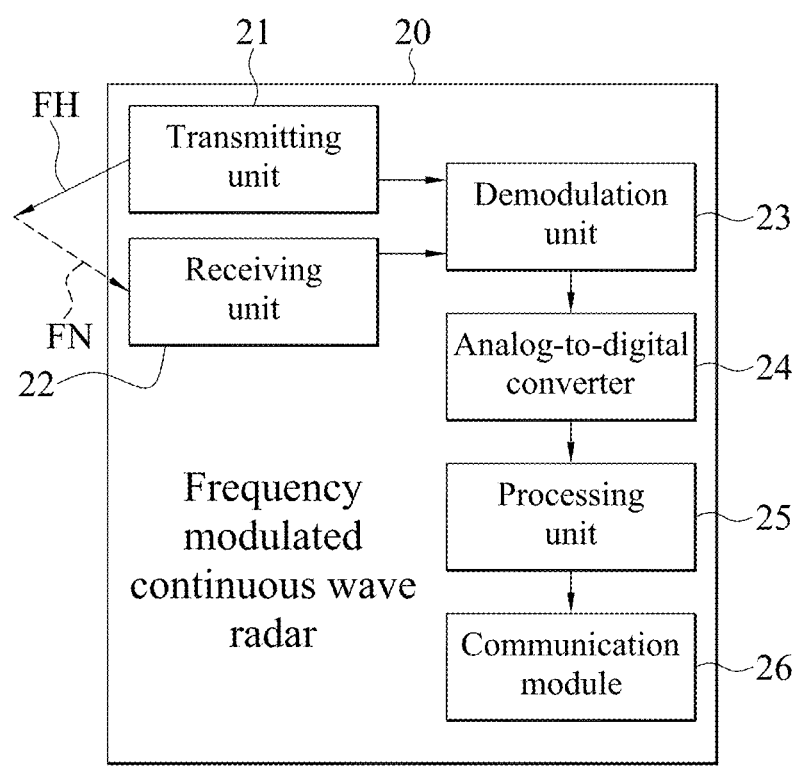
FIG. 21 is a schematic block diagram of an FMCW radar according to some embodiments.

Refer to FIG. 21. FIG. 21 is a schematic block diagram of an FMCW radar 20 according to some embodiments. FMCW radar 20 includes a transmitting unit 21, a receiving unit 22, a demodulation unit 23, an analog-to-digital converter 24, a processing unit 25, and a communication module 26. The transmitting unit 21, the receiving unit 22, the demodulation unit 23, the analog-to-digital converter 24 and the processing unit 25 are the same as the transmitting unit 11, the receiving unit 12, the demodulation unit 13, the analog-to-digital converter 14 and the processing unit 15, and therefore the descriptions are not repeated. The communication module 26 connects to the processing unit 25. In an embodiment, the communication module 26 transmits the digital signal SD outputting from the analog-to-digital converter 24 to another device or a cloud server for further processing. In some another embodiment, the processing unit 25 processes some of the digital signals SD from the analog-to-digital converter 24, and processing results of some of the digital signals are transmitted to the another device or the cloud server through the communication module 26 for further processing. The communication module 26 may be, for example, a wired communication interface such as Universal Asynchronous Receiver Transmitter (UART)/Integrated Circuit Bus ($I^2C$)/Serial Peripheral Interface (SPI)/Controller Area Network (CAN)/Recommended Standard (RS) 232/Recommended Standard (RS) 422, etc. The communication module 26 may be, for example, but not limited to, a wireless communication interface such as a wireless sensor network (eg, EnOcean/Bluetooth/ZigBee), a cellular network (2G/3G/Long Term Evolution (LTE)/5G), Wireless Local Area Network (for example, Wireless Local Area Network (WLAN)/World Interoperability for Microwave Connectivity (WiMAX)), short-range point-to-point communication (for example, Radio Frequency Identification (RFID)/EnOcean/Near Field Communication (NFC)), etc.

Referring to FIG. 4, a frequency $f_0$ of the intermediate frequency signal SI may be expressed as Equation 1, where S is a slope, and $\tau$ is a delay time between transmitting the incident radar signal FH and receiving the reflected radar signal FN. Therefore, $\tau$ may be expressed as Equation 2, where d is a distance between the transmitting antenna of the radar and the target 90, and c is the speed of light. Equation (3) can be obtained by substituting Equation (2) into Equation (1). It can be known from Equation 3 that the frequency $f_0$ of the intermediate frequency signal SI implies distance information (that is, a distance between the FMCW radar 10' and the target 90).

$$f_0 = S\tau \qquad \text{Equation 1}$$

$$\tau = 2d/c \qquad \text{Equation 2}$$

$$f_0 = 2Sd/c \qquad \text{Equation 3}$$

Figure 5:
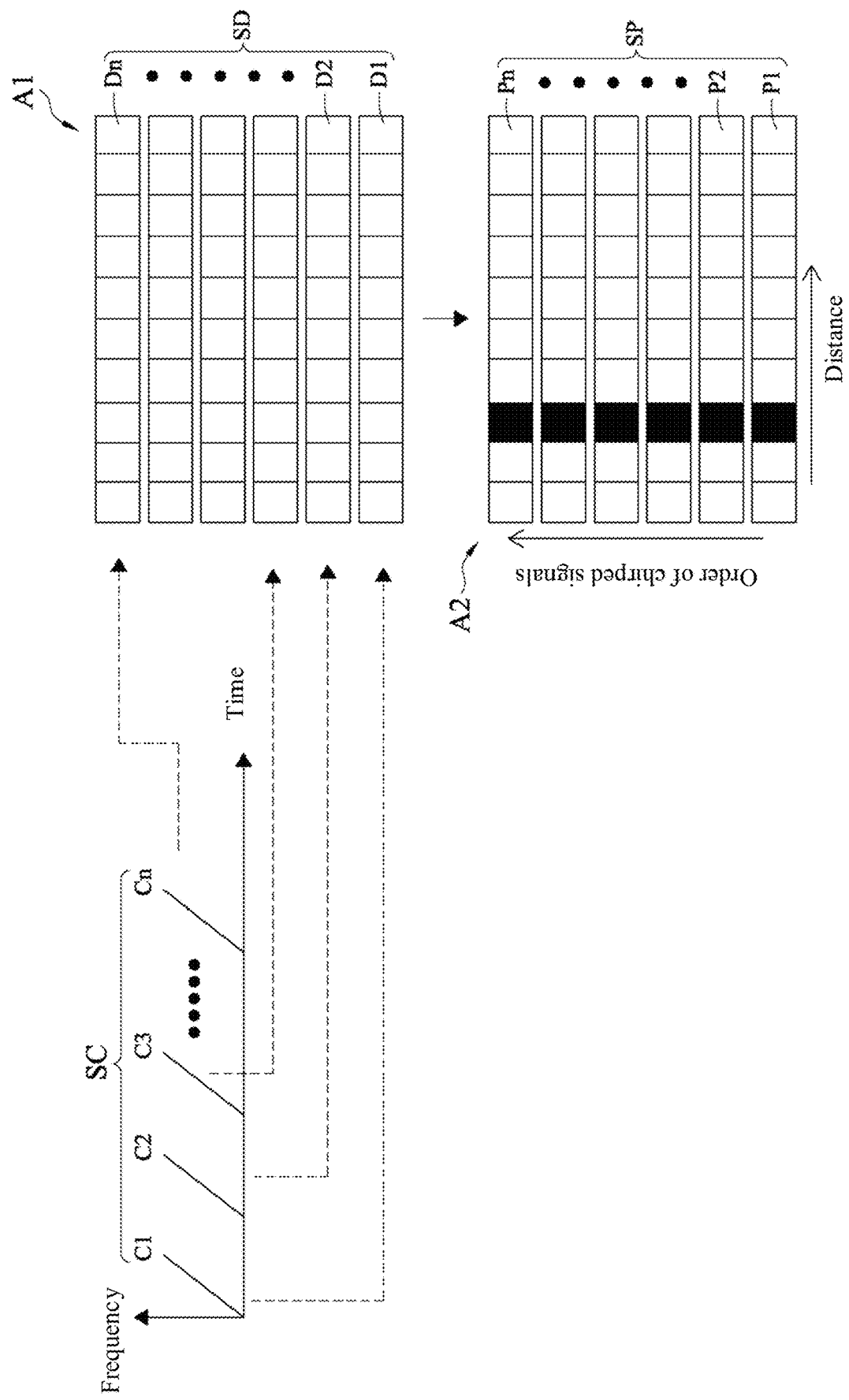
FIG. 5 is a schematic diagram of signal processing according to some embodiments.

FIG. 5 is a schematic diagram of signal processing according to some embodiments. Chirped pulses SC are respectively numbered as C1, C2, C3, . . . , and Cn in sequence, where n is a positive integer. The analog-to-digital converter 14 converts received intermediate frequency signals SI corresponding to the chirped pulses C1 to Cn into digital signals SD (which are respectively expressed as sequences D1, D2, . . . , and Dn, n being a positive integer), and each chirped pulse Cx (x=1 to n) corresponds to a sequence Dx (x=1 to n). Each sequence Dx (x=1 to n) of the digital signals SD may be expressed as a one-dimensional array (a row matrix). The transverse arrays Dx (x=1 to n) are arranged longitudinally in sequence to form a two-dimensional matrix A1. It can be understood that the digital signals SD may alternatively be arranged to form column arrays, and the column arrays are arranged transversely in sequence. Similarly, another two-dimensional matrix can be obtained. Values of the two-dimensional matrix A1 represent signal strengths (amplitudes). An index value x of a column of the two-dimensional matrix A1 corresponds to an order of the chirped pulses SC. An index value of a row of the two-dimensional matrix A1 has the meaning of time. That is, the row array of the two-dimensional matrix A1 is a time-domain signal (a set of digital data related to time).

The processing unit 15 performs FFT (which is hereinafter referred to as "distance Fourier transform") on the row arrays of the two-dimensional matrix A1 (that is, the two-dimensional matrix A1 formed by the digital signals SD) to obtain frequency-domain signals SP (which are respectively expressed as P1, P2, . . . , and Pn, n being a positive integer), that is, the two-dimensional matrix A2. Therefore, the row arrays of the two-dimensional matrix A2 are equivalent to a frequency spectrum distribution in response to a chirped pulse Cx. As described above, the frequency of the intermediate frequency signal SI implies distance information. That is, an index value of a row of the two-dimensional matrix A2 has the meaning of distance. Values of the two-dimensional matrix A2 represent intensities of frequencies on a frequency spectrum, which can present strengths of radar signals reflected at different distances from the FMCW radar 10'. As shown in FIG. 5, a colored box in the two-dimensional matrix A2 is a peak (that is, a value exceeds a threshold), which indicates that there is a target 90 at a distance corresponding to the frequency. A distance between the FMCW radar 10' and the target 90 can be calculated according to the frequency at the peak. Further, wide-range exercise information (such as an average speed) can be obtained through calculation according to specific distance changes of the target 90 calculated at different time points.

Descriptions are made above by using an example in which the transmitting unit 11 has one transmitting antenna and the receiving unit 12 has one receiving antenna. However, the transmitting unit 11 has a plurality of transmitting antennas to transmit a plurality of incident radar signals FH, and the receiving unit 12 has a plurality of receiving antennas to respectively receive reflected radar signals FN, to perform beamforming.

Figure 6:
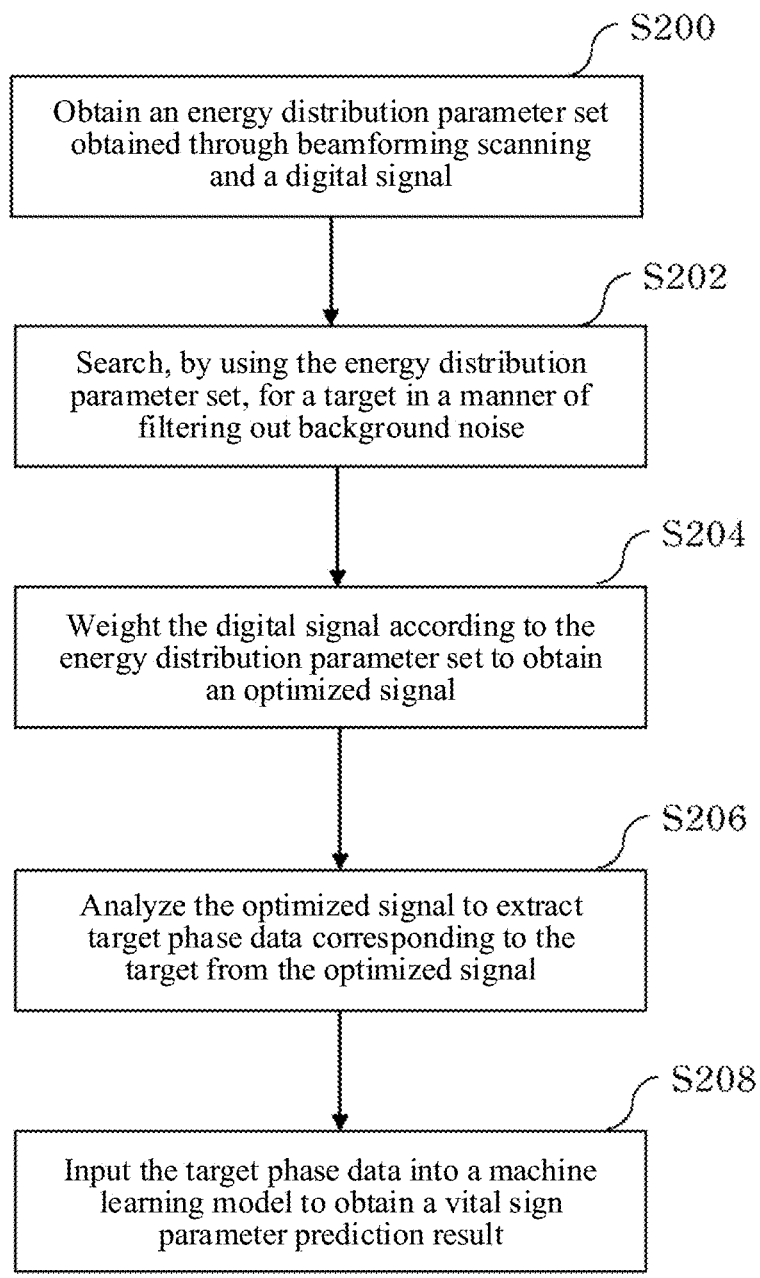
FIG. 6 is a flowchart of a data pre-processing method according to some embodiments.
Figure 7:
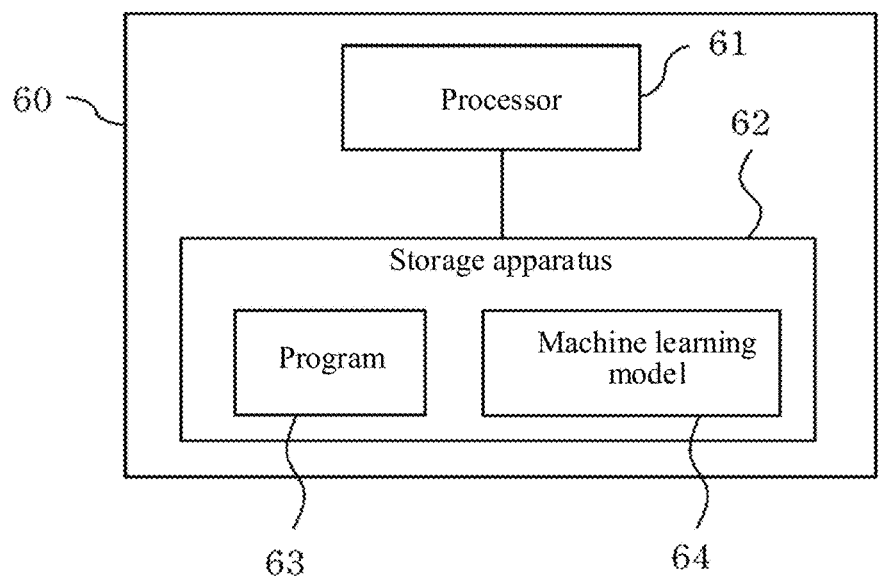
FIG. 7 is a schematic block diagram of a signal processing apparatus according to some embodiments.

Refer to FIG. 6 and FIG. 7 together. FIG. 6 is a flowchart of a radar signal data pre-processing method according to some embodiments, which describes a data pre-processing process that can be applied to a machine learning model for vital sign parameter prediction. FIG. 7 is a schematic block diagram of a signal processing apparatus 60 according to some embodiments. The signal processing apparatus 60 includes a processor 61 and a storage apparatus 62. The storage apparatus 62 is a computer-readable storage medium for storing a program 63 executed by the processor 61 to perform the data pre-processing method. In some embodiments, the signal processing apparatus 60 is the foregoing FMCW radar 10', and the processor 61 is the foregoing processing unit 15. In some embodiments, the signal processing apparatus 60 is an edge apparatus or a cloud server. That is, after obtaining the digital signal SD, the FMCW radar 10' transmits the digital signal SD to the edge apparatus or the cloud server, and the edge apparatus or the cloud server performs digital signal processing on the digital signal SD.

Figure 8:
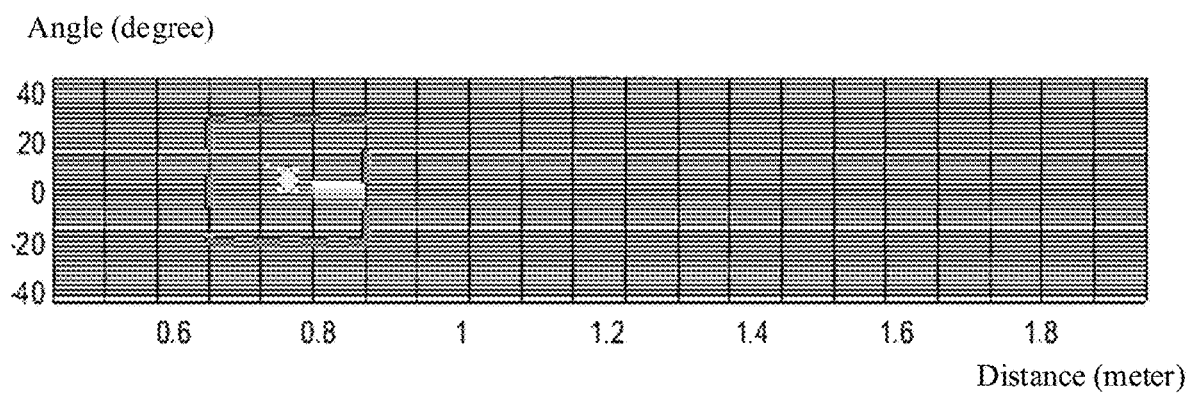
FIG. 8 is a spectral signal intensity diagram in a two-dimensional space according to some embodiments.

In step S200, as described above, the analog-to-digital converter 14 may convert the received intermediate frequency signals SI corresponding to the chirped pulses Cx into the digital signals SD, and therefore, the processor 61 can obtain a digital signal SD corresponding to the reflected radar signal FN. In addition, after receiving the digital signal SD, the FMCW radar 10' scans a field in a beamforming manner and calculates signal intensities at different distances and azimuth angles, to obtain an energy distribution parameter set. The energy distribution parameter set includes parameters such as angles, distances, and power, and a spectral signal intensity diagram in a two-dimensional space can be established accordingly. FIG. 8 is a spectral signal intensity diagram in a two-dimensional space according to some embodiments. The transverse axis represents a distance, and the longitudinal axis represents an angle. The magnitude of power (energy intensity) is presented by color depth herein. In addition to FFT, the beamforming algorithm may alternatively be another adaptive beamforming method, for example, MUltiple SIgnal Classification (MUSIC), Capon, estimation of signal parameters via rotational invariance techniques (ESPRIT), or the conventional beamforming (CBF) algorithm.

In step S202, the target 90 is searched for, by using the energy distribution parameter set, in the field in a manner of filtering out background noise. The manner of filtering out background noise may be, for example, a constant false alarm rate (CFAR) filtering method. If a peak (shown by a dashed box in FIG. 8) is found through such a calculation, it indicates that there is the target 90.

In step S204, the digital signal SD is weighted according to the energy distribution parameter set to obtain an optimized signal, as shown in Equation 4. Yk is the optimized signal, Xs is the digital signal, and $w_k$ (r,θ) is a weight calculated according to such parameters as a distance r and an angle θ. A weight may be calculated by substituting such parameters as the distance r and the angle θ in the energy distribution parameter set into a Capon Beamforming weight formula. In this way, a signal in a specific region (that is, a region adjacent to the target 90) may be optimized to improve a signal-to-noise ratio.

$$Y_k = X_s \cdot w_k(r,\theta) \qquad \text{Equation 4}$$

In step S206, the optimized signal may be analyzed to extract target phase data corresponding to the target 90. After the target phase data is obtained, the target phase data may be inputted into a machine learning model 64 to predict a vital sign parameter (step S208). For example, a corresponding respiratory rate or heart rate is predicted. In some embodiments, the target phase data is normalized and then inputted into the machine learning model 64. In an embodiment, the machine learning model 64 is a MobileNetV3 model. Usage samples are acquired usage data of two types of sports equipment (bicycle and elliptical machine). 30 person-pieces of radar data are collected for each type of sports equipment, and there are a total of 60 person-pieces of radar data, where 50 person-pieces of radar data are used for training, and 10 person-pieces of radar data are used for prediction. Each piece of radar data includes data of four exercise intensities (at rest, slow, moderate, and fast), and each exercise intensity lasts for two minutes. The FMCW radar 10' is mounted at a height of 1 to 2.5 meters and at a distance of 0.5 to 1.5 meters from a subject. However, the present invention is not limited thereto. During collection, the subject wears a cardiotachometer to obtain a real-time heart rate synchronously as a labeled sample. Subsequently, how to analyze the optimized signal to obtain the target phase data is described first.

Figure 9:
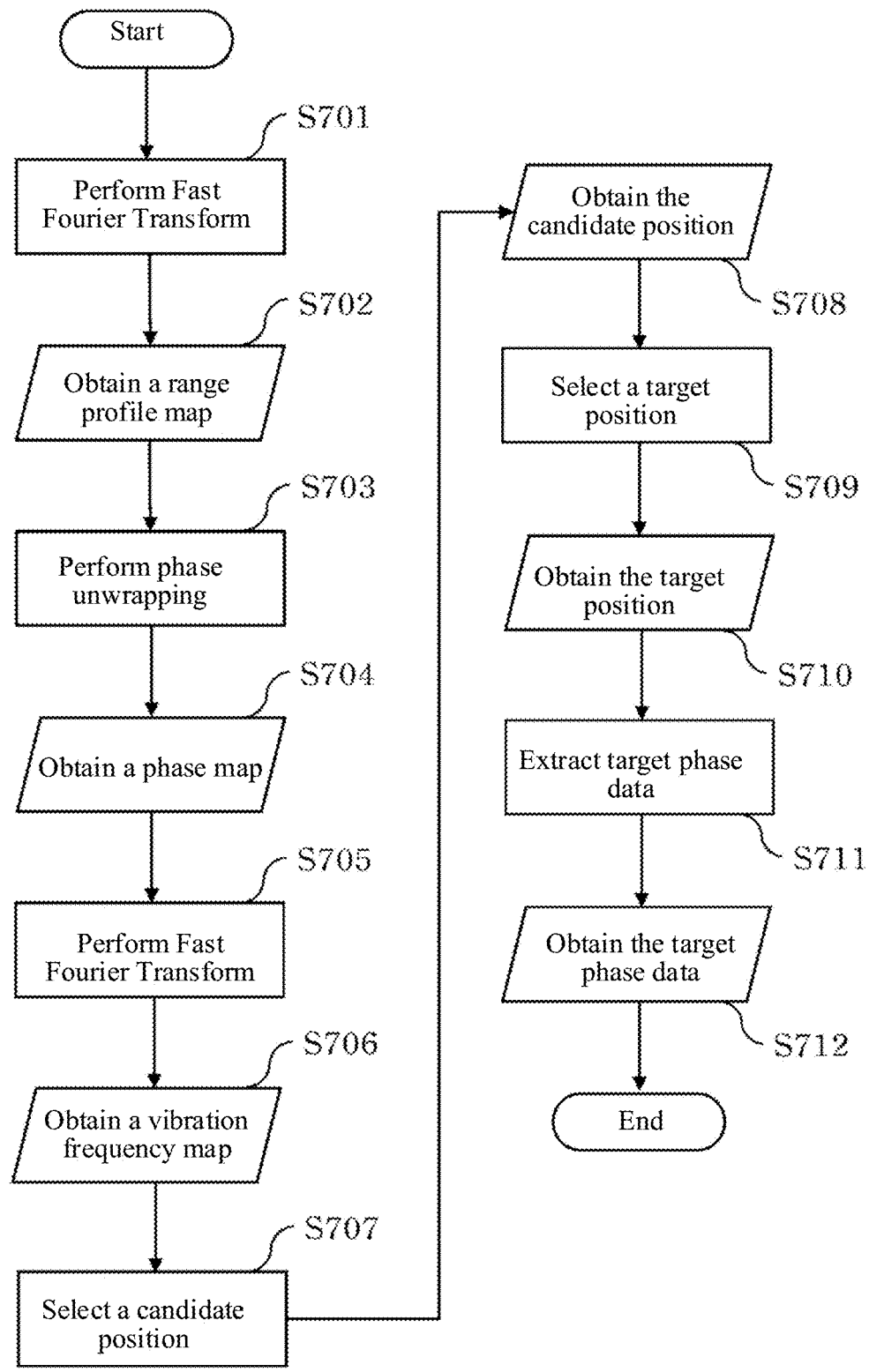
FIG. 9 is a flowchart of signal analysis according to some embodiments.
Figure 10:
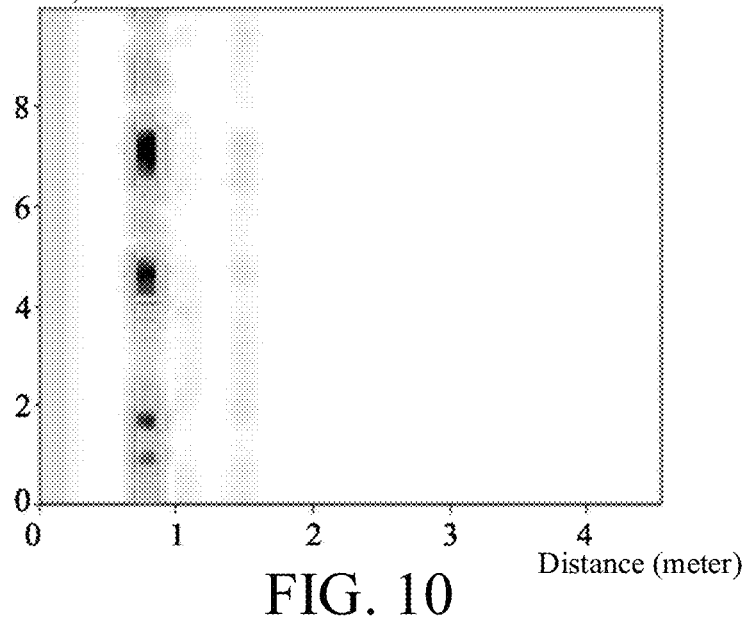
FIG. 10 is a schematic diagram of a range profile map according to some embodiments.

FIG. 9 is a flowchart of signal analysis according to some embodiments. First, in step S701, the foregoing distance Fourier transform is performed on the optimized signal so that a range profile map can be obtained (step S702). FIG. 10 is a schematic diagram of a range profile map according to some embodiments. The range profile map presents an energy distribution with a distance change (transverse axis) and a time change (longitudinal axis) relative to the FMCW radar 10', and an energy difference is presented by color depth herein.

Figure 11:
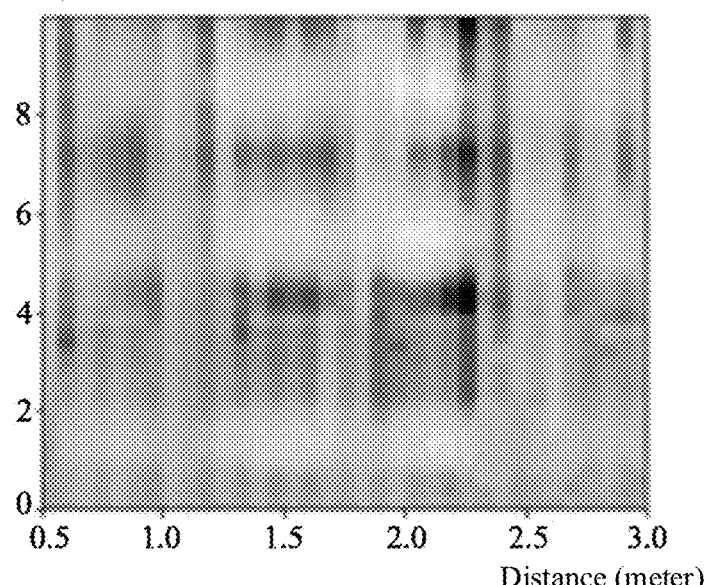
FIG. 11 is a schematic diagram of a phase map according to some embodiments.

According to the optimized signal, in addition to the range profile map, a phase map and a vibration frequency map can be further obtained. In step S703, direct current (DC) bias removal (DC removal), in-phase and quadrature-phase (IQ) imbalance compensation (ellipse correction), arctangent, and phase unwrapping are performed on the range profile map to obtain a phase map (step S704). FIG. 11 is a schematic diagram of a phase map according to some embodiments. The phase map presents an energy distribution with a distance change (transverse axis) and a phase change (longitudinal axis) relative to the FMCW radar 10', and an energy difference is presented by color depth herein.

Figure 12:
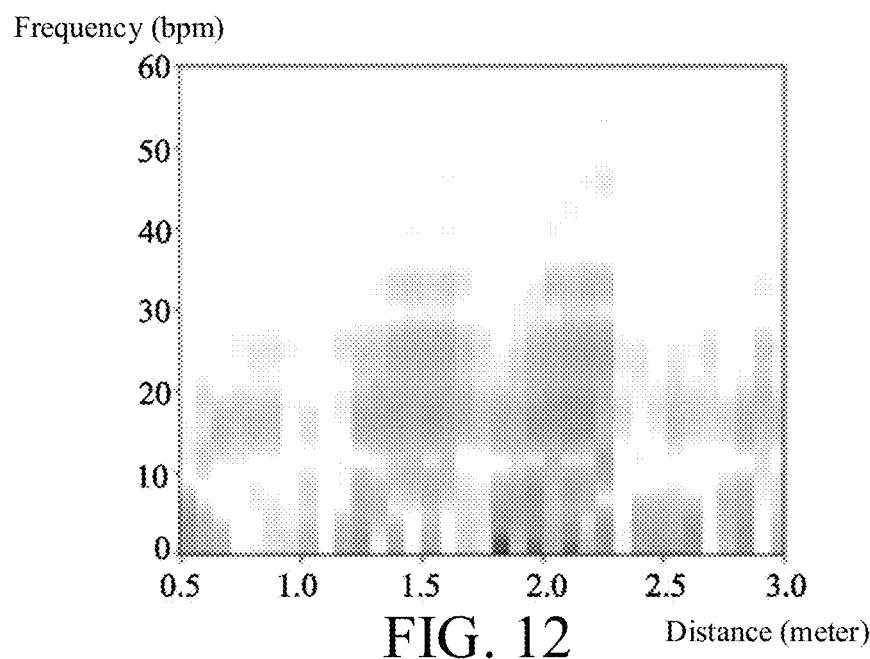
FIG. 12 is a schematic diagram of a vibration frequency map according to some embodiments.

Subsequently, in step S705, FFT is performed on phase distributions (that is, range bins) on ranges on the phase map to obtain a vibration frequency map (step S706). FIG. 12 is a schematic diagram of a vibration frequency map according to some embodiments. The vibration frequency map presents an energy distribution with a distance change (transverse axis) and a vibration frequency change (longitudinal axis) relative to the FMCW radar 10', and an energy difference is presented by color depth herein.

Figure 13:
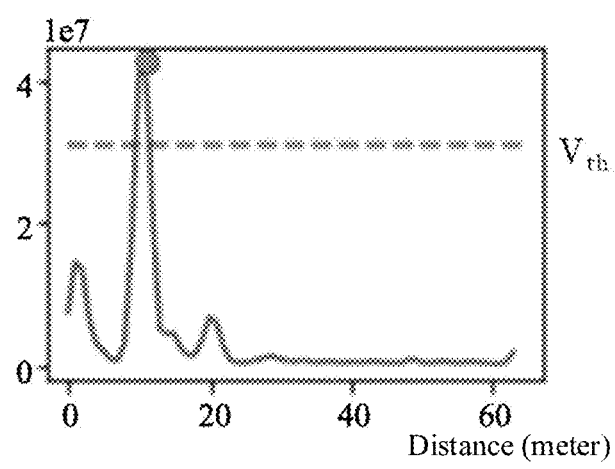
FIG. 13 is a schematic diagram of a vibration frequency distribution of range bins according to some embodiments.

After the vibration frequency map is obtained, in step S707, at least one candidate position having an energy intensity exceeding an energy threshold is selected from the vibration frequency map (step S708). FIG. 13 is a schematic diagram of a vibration frequency distribution of range bins according to some embodiments. FIG. 13 presents a peak exceeding the energy threshold $V_{th}$, and therefore, the range bin is selected as a candidate position. In other words, in step S707, each range bin in the phase map is compared with the energy threshold $V_{th}$. If the energy threshold $V_{th}$ is exceeded, the corresponding range bin is selected as a candidate position.

In some embodiments, the energy threshold $V_{th}$ is a floating threshold. The energy threshold $V_{th}$ is calculated for each range bin in the phase map. The energy threshold $V_{th}$ is determined according to an average energy value or a maximum energy value of the corresponding range bin. For example, the energy threshold $V_{th}$ is a sum of a times the average energy value and b times the maximum energy value, a+b=1, and a and b are positive numbers. In another example, the energy threshold $V_{th}$ is a times the average energy value, and a is a positive number.

There may be a plurality of candidate positions obtained in the foregoing step S708. Therefore, it is necessary to further determine which one should be selected to eliminate interference signals. In step S709, one or more candidate positions are selected from the candidate positions to obtain one or more target positions (step S710). The target position is a position having a vibration frequency meeting a vital sign parameter range in the candidate positions. The vital sign parameter range may be, for example, a respiratory rate range (such as 10 to 20 breaths per minute), or a heart rate range (such as 60 to 100 beats per minute (bpm)).

Specifically, in some embodiments, there is one target 90 in a detection field. Candidate positions having the vibration frequency meeting the vital sign parameter range are found out, and one of the candidate positions that has the highest energy intensity in a vibration frequency range is selected. The selected candidate position (distance) is a position (that is, the target position) of the target 90.

In some embodiments, there are a plurality of targets 90 in the detection field. N to-be-detected target positions are selected from the candidate positions, where N is greater than 1. The N to-be-detected target positions are positions that have the vibration frequency meeting the vital sign parameter range in the candidate positions and have top N energy intensities. The to-be-detected target positions are positions (that is, the target positions) of the targets 90.

After one or more positions of one or more targets are determined, corresponding one or more pieces of target phase data can be extracted accordingly (step S711). It is taken into consideration that a misjudgment may be generated during detection of an object in an exercise state to cause a deviation. In step S711, a piece of target phase data in a corresponding distance range in the phase map is obtained according to each target position (step S712). In some embodiments, one piece of target phase data in a corresponding distance range in the phase map is obtained according to each target position. The target phase data includes a range bin of the target position. In some other embodiments, a plurality of pieces of target phase data in a corresponding distance range in the phase map are obtained according to each target position. The pieces of target phase data further include one or more range bins adjacent to the target position in addition to a range bin of the target position. For example, two range bins on either side are taken by using the range bin of the target position as a center, and the target phase data includes five range bins.

The content of the foregoing step S208 is described herein. In step S208, the target phase data of each to-be-detected target position is inputted into the machine learning model 64, to obtain a vital sign parameter prediction result. For example, a corresponding respiratory rate or heart rate is predicted. In some embodiments, the target phase data is normalized and then inputted into the machine learning model 64.

Figure 14:
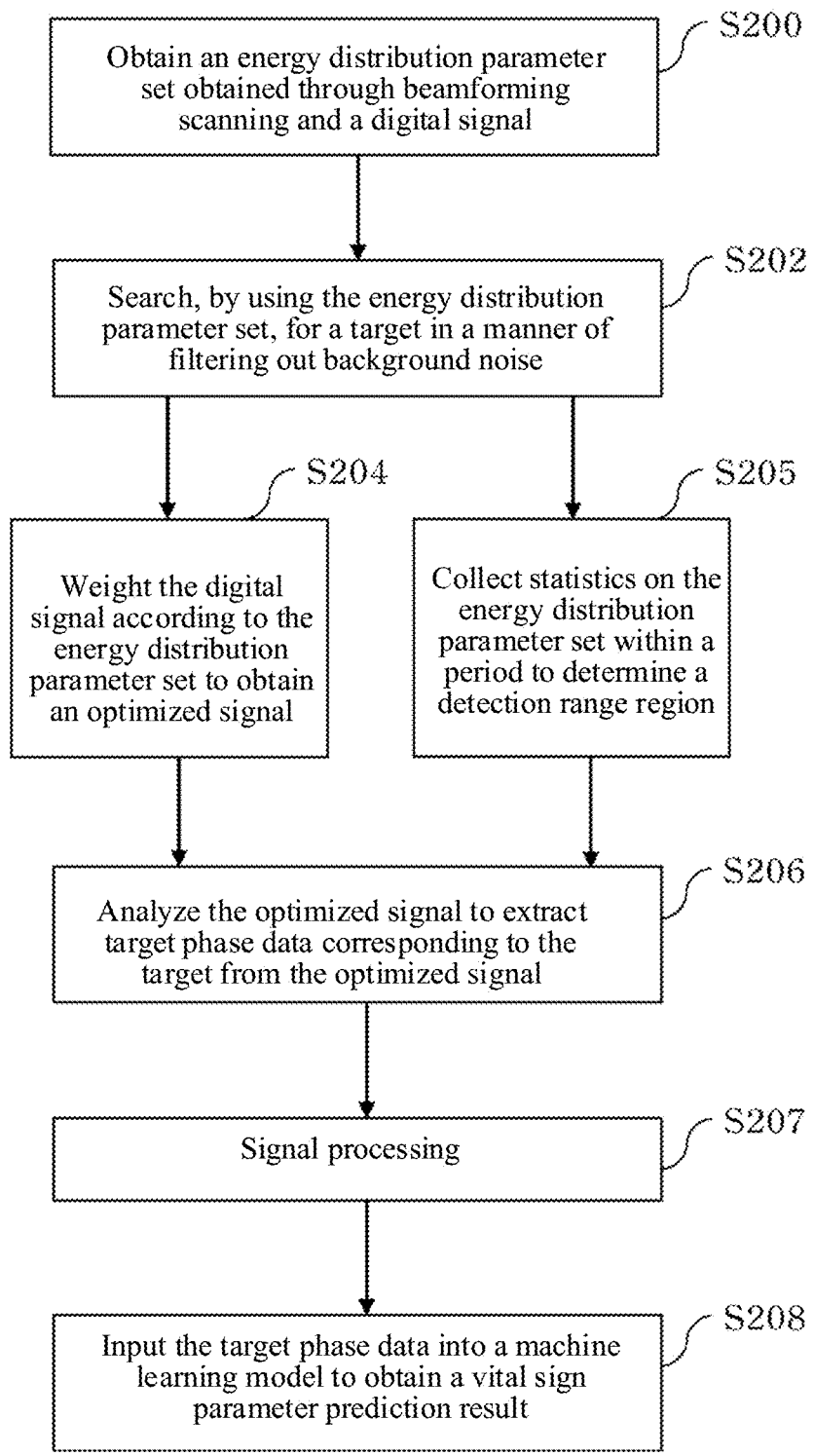
FIG. 14 is a flowchart of another data pre-processing method according to some embodiments.

FIG. 14 is a flowchart of another data pre-processing method according to some embodiments. Compared with FIG. 6, step S205 is further included before step S206. In step S205, statistics on the energy distribution parameter set within a period (for example, 10 to 20 seconds) may be continuously collected to analyze an activity state of the target 90, and determine a detection range region (a bounding box) covering an activity range of the target 90 accordingly, for example, a dashed box shown in FIG. 8. Accordingly, in step S206, analysis may be performed only on the optimized signal in the detection range region (in a specific range). That is to say, in the foregoing step S707, only range bins within the detection range region need to be monitored, and the candidate position is selected from the detection range region in the vibration frequency map. In this way, a calculation amount can be reduced, and calculation time can be saved. The detection range region may be updated regularly (for example, every 30 seconds). An update cycle may be dynamically adjusted according to an analyzed perturbation rate of the target 90 in the detection range region. For example, when the target 90 sways violently during an activity, the update cycle may be shortened. Correspondingly, when the target 90 sways moderately during an activity, the update cycle may be extended to reduce the calculation complexity. In some other embodiments of the present invention, a plurality of detection range regions may be selected to meet requirements in multi-target detection.

Figure 15:
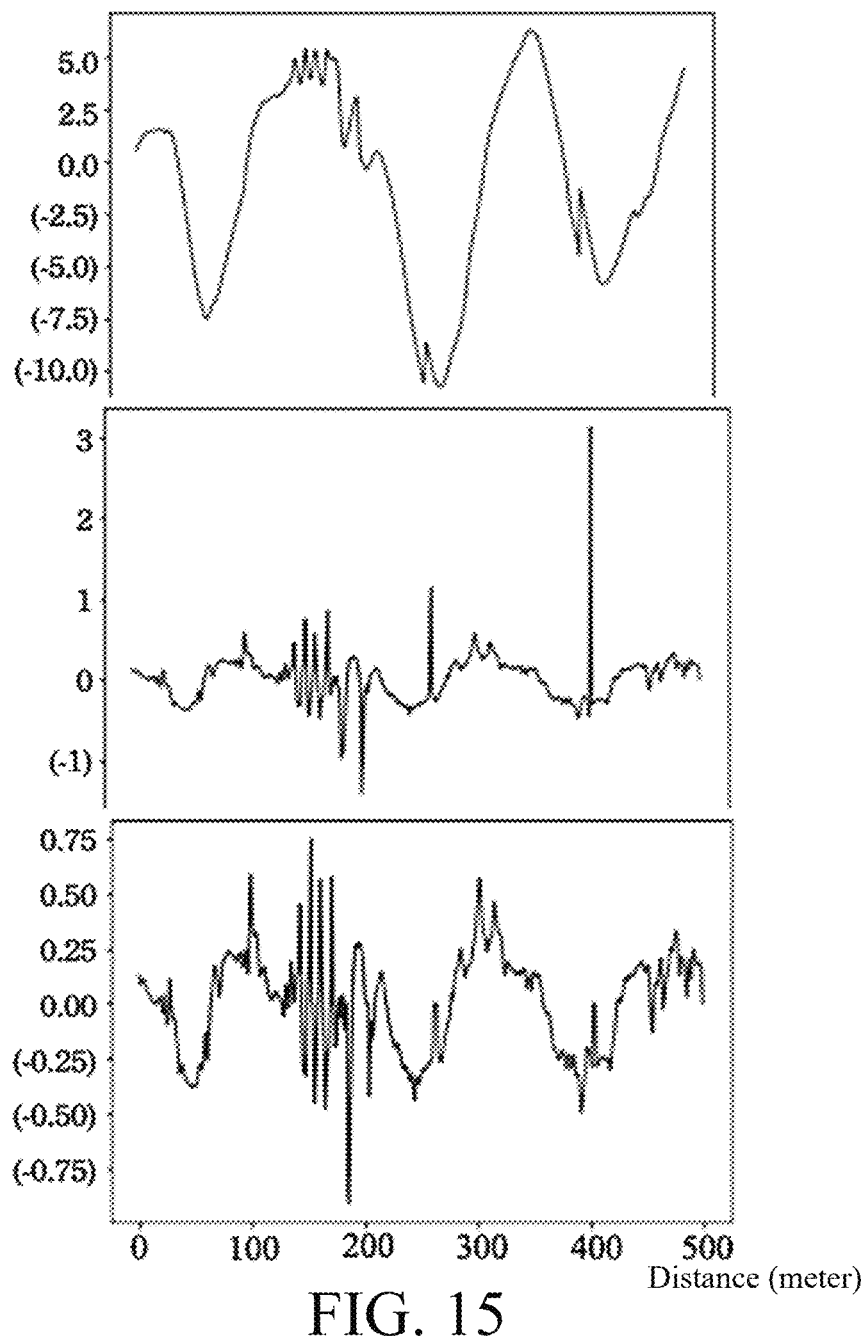
FIG. 15 is a schematic diagram of signal processing according to some embodiments.

In some embodiments, as shown in FIG. 14, compared with FIG. 6, before step S208 is performed, signal processing is further performed on the target phase data first (step S207). FIG. 15 is a schematic diagram of signal processing according to some embodiments. An upper figure in FIG. 15 is a schematic diagram of a range bin, and a middle figure in FIG. 15 is presented after phase difference calculation. The phase difference calculation refers to a subtraction between two adjacent values. Next, after pulse noise removal, a lower figure in FIG. 15 is presented. A specific practice may be that, for example, when the phase difference is excessively large and exceeds a preset threshold, the phase difference is replaced with 0. In this way, noise interference can be reduced.

Figure 16:
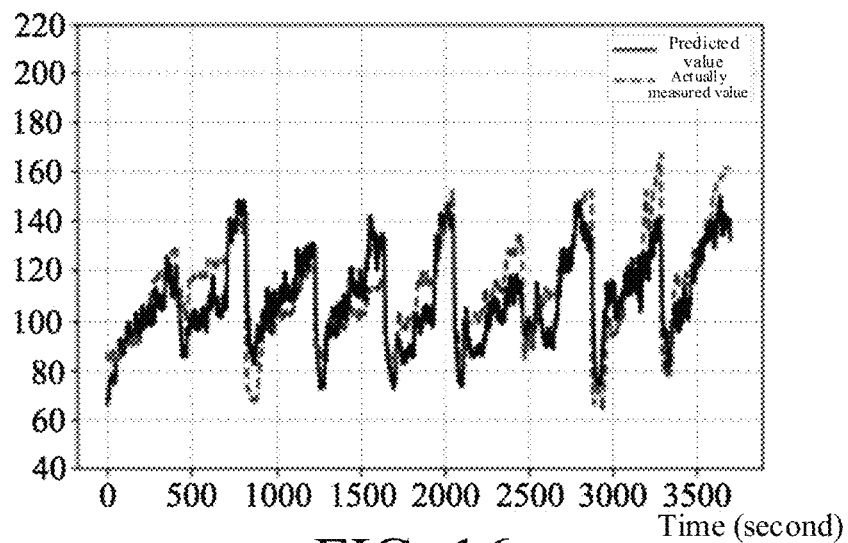
FIG. 16 is a schematic diagram of a vital sign parameter prediction result obtained by performing a process shown in FIG. 14.
Figure 17:
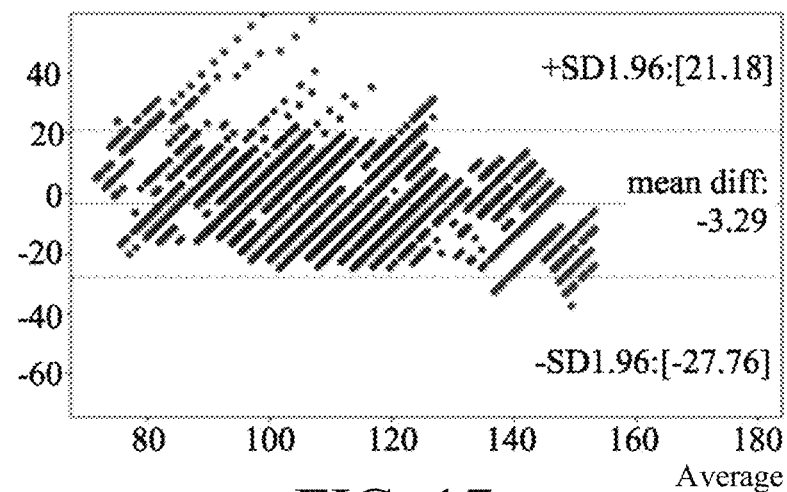
FIG. 17 is a Bland-Altman plot according to some embodiments.

FIG. 16 is a schematic diagram of a vital sign parameter prediction result obtained by performing a process shown in FIG. 14. An accuracy rate is 90.49%, a root-mean-square error is 12.72 (bpm), and a standard error is 7.43 (bpm). It can be seen that, predicted heart rate changes are consistent with actual heart rate changes, which can effectively determine the exercise intensity. As a comparison, if the digital signal SD rather than the optimized signal is used for performing the process shown in FIG. 9 to input the target phase data into the machine learning model 64 (signal processing in step S207 is not performed), the accuracy rate is 86.88%, the root-mean-square error is 20.04 (bpm), and the standard error is 14.69 (bpm). It can be seen that the accuracy rate of the prediction result is increased by about 4% in some embodiments of the present invention. FIG. 17 is a Bland-Altman plot according to some embodiments, to determine, through comparison, a difference between prediction results in such two practices.

Figure 18:
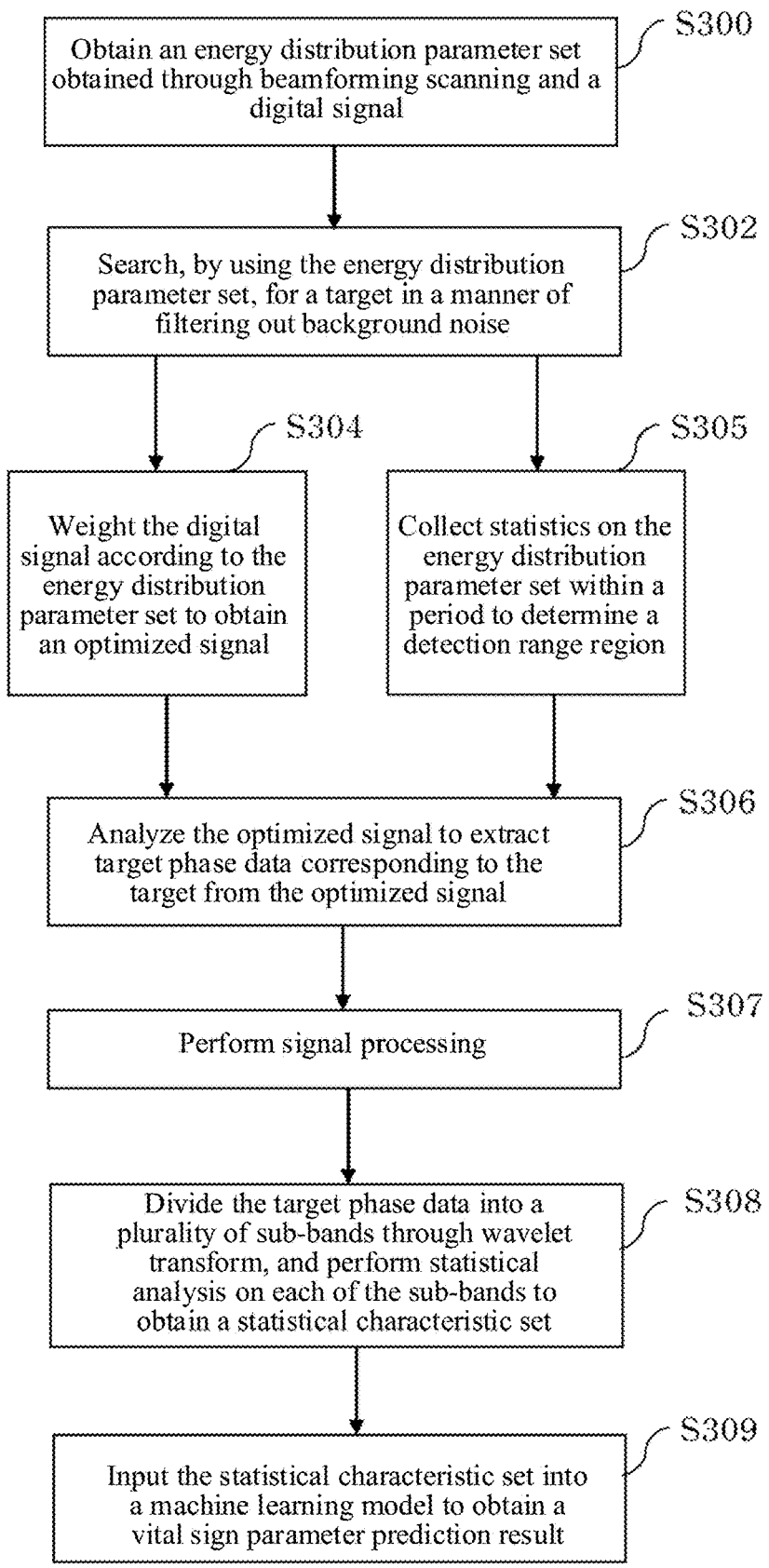
FIG. 18 is a flowchart of still another data pre-processing method according to some embodiments.

FIG. 18 is a flowchart of still another data pre-processing method according to some embodiments. Compared with FIG. 14, steps S300 to S307 are substantially the same as the foregoing steps S200 to S207. A difference lies in that in this embodiment, the target phase data is not directly inputted into the machine learning model 64. In step S308, each range bin in the target phase data is divided into a plurality of sub-bands through wavelet transform, and statistical analysis is performed on each of the sub-bands to obtain a statistical characteristic set. For example, for each of the sub-bands, statistics are collected on a total of 14 statistical characteristics such as entropy, skewness, kurtosis, a variance, a standard deviation, a mean, a median, the $5^{th}$ percentile value, the $25^{th}$ percentile value, the $75^{th}$ percentile value, the $95^{th}$ percentile value, a root mean square value, a zero crossing rate, and a mean crossing rate. If a fifth-order wavelet decomposition is performed to obtain a total of 6 sub-bands, the data amount of a range bin may be reduced to 84 characteristic parameters from 500 characteristic parameters. In this way, the calculating burden can be reduced.

Figure 19:
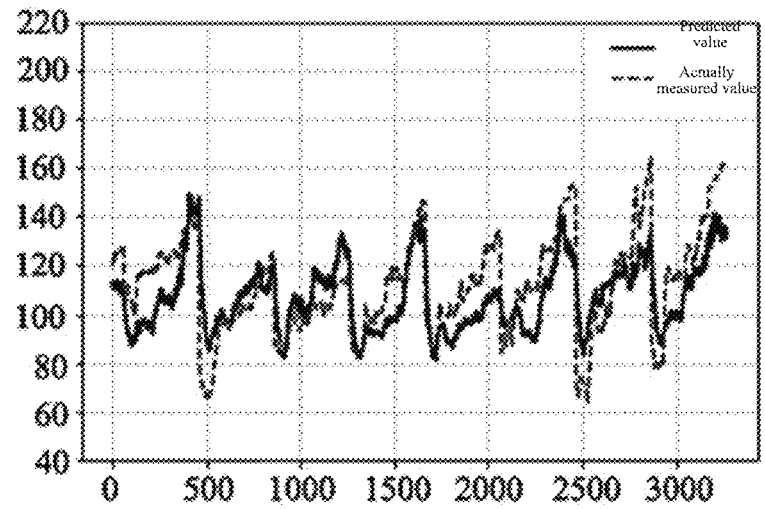
FIG. 19 is a schematic diagram of a vital sign parameter prediction result obtained by performing a process shown in FIG. 18.
Figure 20:
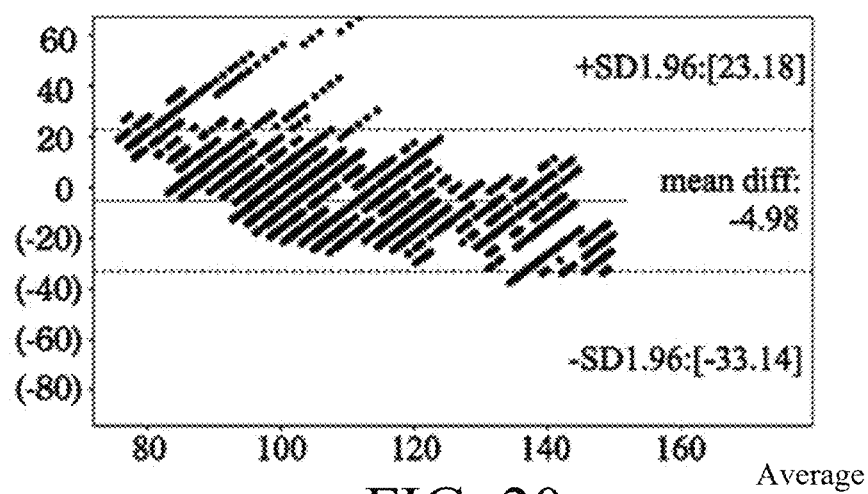
FIG. 20 is a Bland-Altman plot according to some embodiments.

In step S309, the statistical characteristic set is inputted into a machine learning model to obtain a vital sign parameter prediction result. FIG. 19 is a schematic diagram of a vital sign parameter prediction result obtained by performing a process shown in FIG. 18. An accuracy rate is 88.76%, a root-mean-square error is 15.02 (bpm), and a standard error is 8.58 (bpm). FIG. 20 is a Bland-Altman plot according to some embodiments, to compare results obtained by performing the processes shown in FIG. 15 and FIG. 18. It can be seen that, although the accuracy rate is slightly poorer, there is not much difference in prediction performance.

In the foregoing non-contact exercise vital sign detection method, the digital signal SD is obtained in a sliding window manner and processed. In some embodiments, a size of a window is 10 seconds, and a time step is one second.

Based on the above, through the radar signal data pre-processing method and the exercise vital sign detection radar 10 according to some embodiments, vital sign parameters can be accurately detected when a subject is in an exercise state and the exercise intensity of the subject can be detected. In some embodiments, by weighting the digital signal, a signal-to-noise ratio can be increased. In some embodiments, by automatically generating the detection range region, calculation complexity can be reduced and an object tracking effect can be improved. In some other embodiments, a plurality of detection range regions are automatically generated to meet requirements in multi-target detection. In some embodiments, through signal processing to reduce noise, noise interference can be reduced. In some embodiments, by performing machine-learning prediction by using the statistical characteristic set, model training and prediction can be accelerated.

What is claimed is:

1. A data pre-processing method, performed by a processor in a signal processing apparatus, the method comprising:
   obtaining an energy distribution parameter set obtained through beamforming scanning and a digital signal, wherein the digital signal corresponds to a reflected radar signal of an exercise vital sign detection radar;
   searching, by using the energy distribution parameter set, for a target in a manner of filtering out background noise;
   weighting the digital signal according to the energy distribution parameter set to obtain an optimized signal;
   determining a detection range region covering an activity range of the target based on statistical analysis of the energy distribution parameter set within a period;
   analyzing the optimized signal only within the detection range region to extract one or more pieces of target phase data corresponding to the target from the optimized signal, wherein the step of analyzing the optimized signal comprises:
      obtaining a phase map and a vibration frequency map according to the optimized signal;
      selecting at least one candidate position having an energy intensity exceeding an energy threshold from the vibration frequency map;
      selecting a target position from the at least one candidate position; and
      obtaining the one or more pieces of target phase data in a distance range in the phase map according to the target position; and
   inputting the one or more pieces of target phase data into a machine learning model to obtain a vital sign parameter prediction result.

2. The data pre-processing method according to claim 1, wherein signal processing is further performed on the one or more pieces of target phase data before the one or more pieces of target phase data are inputted into the machine learning model, wherein the signal processing comprises: phase difference calculation and pulse noise removal.

3. The data pre-processing method according to claim 1, wherein the phase map presents an energy distribution with a distance change relative to the exercise vital sign detection radar and a phase change, and the vibration frequency map presents an energy distribution with the distance change relative to the exercise vital sign detection radar and a vibration frequency change, wherein the target position is a position that has a vibration frequency meeting a vital sign parameter range in the at least one candidate position and has the highest energy intensity.

4. The data pre-processing method according to claim 3, further comprising:
   collecting statistics on the energy distribution parameter set in a period to determine a detection range region covering an activity range of the target, wherein the step of selecting the at least one candidate position is selecting the at least one candidate position from the detection range region in the vibration frequency map.

5. The data pre-processing method according to claim 3, wherein the step of obtaining the phase map and the vibration frequency map comprises:
   performing Fast Fourier Transform (FFT) on the optimized signal to obtain a range profile map, wherein the range profile map presents an energy distribution with the distance change relative to the exercise vital sign detection radar and a time change;
   performing direct current (DC) bias removal, in-phase and quadrature-phase (IQ) imbalance compensation, arctangent, and phase unwrapping on ranges on the range profile map with the time change to obtain the phase map; and performing FFT on phase distributions on ranges on the phase map to obtain the vibration frequency map.

6. The data pre-processing method according to claim 3, wherein the step of selecting the at least one candidate position from the vibration frequency map comprises:

calculating the energy threshold for each range bin in the phase map, wherein the energy threshold is determined according to an average energy value or a maximum energy value of the corresponding range bin; and separately comparing energy values of phases on the each range bin with the energy threshold corresponding to the range bin, to select the at least one candidate position having an energy intensity exceeding the energy threshold.

7. An exercise vital sign detection radar, comprising:

a transmitting unit, configured to transmit an incident radar signal;

a receiving unit, configured to receive a reflected radar signal; and a signal processing module, configured to control the transmitting unit and the receiving unit to perform beamforming scanning to obtain an energy distribution parameter set, obtain a corresponding digital signal according to the reflected radar signal, search, by using the energy distribution parameter set, for a target in a manner of filtering out background noise, weight the digital signal according to the energy distribution parameter set to obtain an optimized signal, determine a detection range region covering an activity range of the target based on statistical analysis of the energy distribution parameter set within a period, analyze the optimized signal to extract one or more pieces of target phase data corresponding to the target from the optimized signal, and input the one or more pieces of target phase data into a machine learning model to obtain a vital sign parameter prediction result, wherein the signal processing module obtains a phase map and a vibration frequency map according to the optimized signal, selects at least one candidate position having an energy intensity exceeding an energy threshold from the vibration frequency map, selects a target position from the at least one candidate position, and obtains the one or more pieces of target phase data in a distance range in the phase map according to the target position.

8. The exercise vital sign detection radar according to claim 7, wherein the signal processing module further performs signal processing on the one or more pieces of target phase data before inputting the one or more pieces of target phase data into the machine learning model, wherein the signal processing comprises: phase difference calculation and pulse noise removal.

9. The exercise vital sign detection radar according to claim 7, wherein the phase map presents an energy distribution with a distance change relative to the exercise vital sign detection radar and a phase change, the vibration frequency map presents an energy distribution with the distance change relative to the exercise vital sign detection radar and a vibration frequency change, and the target position is a position that has a vibration frequency meeting a vital sign parameter range in the at least one candidate position and has the highest energy intensity.

10. The exercise vital sign detection radar according to claim 9, wherein the signal processing module collects statistics on the energy distribution parameter set in a period to determine a detection range region covering an activity range of the target to select the at least one candidate position from the detection range region in the vibration frequency map.

11. The exercise vital sign detection radar according to claim 9, wherein the signal processing module performs Fast Fourier Transform (FFT) on the optimized signal to obtain a range profile map, performs direct current (DC) bias removal, in-phase and quadrature-phase (IQ) imbalance compensation, arctangent, and phase unwrapping on ranges on the range profile map with the time change to obtain the phase map, and performs FFT on phase distributions on ranges on the phase map to obtain the vibration frequency map, wherein the range profile map presents an energy distribution with the distance change relative to the exercise vital sign detection radar and a time change.

12. The exercise vital sign detection radar according to claim 9, wherein the signal processing module calculates the energy threshold for each range bin in the phase map, and separately compares energy values of phases on the each range bin with the energy threshold corresponding to the range bin, to select the at least one candidate position having an energy intensity exceeding the energy threshold, wherein the energy threshold is determined according to an average energy value or a maximum energy value of the corresponding range bin.

13. A data pre-processing method, performed by a processor in a signal processing apparatus, the method comprising:

obtaining an energy distribution parameter set obtained through beamforming scanning and a digital signal, wherein the digital signal corresponds to a reflected radar signal of an exercise vital sign detection radar;

searching, by using the energy distribution parameter set, for a target in a manner of filtering out background noise;

determining a detection range region covering an activity range of the target based on statistical analysis of the energy distribution parameter set within a period;

analyzing the digital signal to extract one or more pieces of target phase data corresponding to the target from the digital signal;

dividing the one or more pieces of target phase data into a plurality of sub-bands through wavelet transform;

performing statistical analysis on each of the sub-bands to obtain a statistical characteristic set; and inputting the statistical characteristic set into a machine learning model to obtain a vital sign parameter prediction result, wherein the step of analyzing the digital signal comprises:

weighting the digital signal according to the energy distribution parameter set to obtain an optimized signal; and analyzing the optimized signal to extract the one or more pieces of target phase data corresponding to the target from the optimized signal, wherein the step of analyzing the optimized signal comprises:

obtaining a phase map and a vibration frequency map according to the optimized signal;

selecting at least one candidate position having an energy intensity exceeding an energy threshold from the vibration frequency map;

selecting at least one target position from the at least one candidate position; and obtaining the one or more pieces of target phase data in a distance range in the phase map according to each target position.

14. The data pre-processing method according to claim 13, wherein the phase map presents an energy distribution with a distance change relative to the exercise vital sign detection radar and a phase change, and the vibration frequency map presents an energy distribution with the distance change relative to the exercise vital sign detection radar and a vibration frequency change, wherein the at least one target position is a position that has a vibration frequency meeting a vital sign parameter range in the at least one candidate position and has the highest energy intensity.

15. The data pre-processing method according to claim 14, wherein the step of selecting the at least one candidate position from the vibration frequency map comprises:

calculating the energy threshold for each range bin in the phase map, wherein the energy threshold is determined according to an average energy value or a maximum energy value of the corresponding range bin; and separately comparing energy values of phases on the each range bin with the energy threshold corresponding to the range bin, to select the at least one candidate position having an energy intensity exceeding the energy threshold.

16. The data pre-processing method according to claim 13, wherein the phase map presents an energy distribution with a distance change relative to the exercise vital sign detection radar and a phase change, and the vibration frequency map presents an energy distribution with the distance change relative to the exercise vital sign detection radar and a vibration frequency change;, wherein the at least one target position is N to-be-detected target positions, wherein N is greater than 1, and the N to-be-detected target positions are positions that have a vibration frequency meeting a vital sign parameter range in the at least one candidate position and have top N energy intensities.

17. The data pre-processing method according to claim 13, wherein signal processing is further performed on the one or more pieces of target phase data before wavelet transform is performed on the one or more pieces of target phase data, wherein the signal processing comprises: phase difference calculation and pulse noise removal.

* * * * *

UNITED STATES PATENT AND TRADEMARK OFFICE
CERTIFICATE OF CORRECTION

| | | |
|---|---|---|
| PATENT NO. | : 12,403,358 B2 | Page 1 of 1 |
| APPLICATION NO. | : 17/678492 | |
| DATED | : September 2, 2025 | |
| INVENTOR(S) | : Kai-Jen Cheng et al. | |

It is certified that error appears in the above-identified patent and that said Letters Patent is hereby corrected as shown below:

On the Title Page

Item (72), please delete the name "Mn-Yu Chen" and insert therefor --Yin-Yu Chen--

In the Claims

Column 12, Lines 15-16, please delete the phrase "only within the detection range region."

Signed and Sealed this
Twenty-third Day of December, 2025

John A. Squires
*Director of the United States Patent and Trademark Office*